US010709627B2

(12) United States Patent
Herrschaft et al.

(10) Patent No.: US 10,709,627 B2
(45) Date of Patent: Jul. 14, 2020

(54) USE OF HIGH PRESSURE LOW VOLUME AIR CONVERSION TO LOW PRESSURE HIGH VOLUME AIR TO POWER PATIENT TRANSPORT DEVICES

(71) Applicant: QFIX SYSTEMS, LLC, Avondale, PA (US)

(72) Inventors: Rich Herrschaft, West Chester, PA (US); James Manning, Newark, DE (US); Barry Hand, Mount Pleasant, SC (US); Daniel Coppens, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 224 days.

(21) Appl. No.: 15/541,800

(22) PCT Filed: Jan. 14, 2016

(86) PCT No.: PCT/US2016/013418
§ 371 (c)(1),
(2) Date: Jul. 6, 2017

(87) PCT Pub. No.: WO2016/115351
PCT Pub. Date: Jul. 21, 2016

(65) Prior Publication Data
US 2018/0008495 A1 Jan. 11, 2018

Related U.S. Application Data

(60) Provisional application No. 62/103,805, filed on Jan. 15, 2015.

(51) Int. Cl.
*A61G 7/10* (2006.01)
*A61B 6/04* (2006.01)
(Continued)

(52) U.S. Cl.
CPC .......... *A61G 7/1028* (2013.01); *A61B 5/0555* (2013.01); *A61B 6/045* (2013.01);
(Continued)

(58) Field of Classification Search
CPC ... A61B 7/1028; A61B 5/0555; A61B 6/0407; A61B 6/0421; A61B 6/045; A61B 17/2255
See application file for complete search history.

(56) References Cited

U.S. PATENT DOCUMENTS 4,528,704 A * 7/1985 Wegener .................. B65G 7/06
180/125
5,065,464 A * 11/1991 Blanchard ............ A61G 7/1028
180/125
(Continued)

OTHER PUBLICATIONS

International Search Report and Written Opinion for International Application PCT/US2016/013418, dated Jul. 21, 2016—12 Pages.
(Continued)

*Primary Examiner* — Robert G Santos
*Assistant Examiner* — Rahib T Zaman
(74) *Attorney, Agent, or Firm* — RatnerPrestia

(57) ABSTRACT

Systems for patient support, imaging, or transport include a modality with a support surface configured to support a patient thereon, a converter associated with the modality, the converter being configured to receive relatively low-volume high-pressure air from a source of the relatively low-volume high-pressure air and to convert the relatively low-volume high-pressure air into relatively high-volume low-pressure air, and an air flow device configured to receive the relatively high-volume low-pressure air from the converter and provide an air flow function to the modality using the relatively high-volume low-pressure air.

22 Claims, 9 Drawing Sheets

(51) Int. Cl.
   *A61B 5/055*     (2006.01)
   *A61B 17/225*    (2006.01)
(52) U.S. Cl.
   CPC .......... *A61B 6/0407* (2013.01); *A61B 6/0421* (2013.01); *A61B 17/2255* (2013.01)

(56) References Cited

U.S. PATENT DOCUMENTS

| | | | | |
|---|---|---|---|---|
| 6,119,292 | A * | 9/2000 | Haas | A61G 7/001 5/713 |
| 7,146,660 | B2 * | 12/2006 | Heimbrock | A61G 7/1026 5/81.1 R |
| 7,555,792 | B2 * | 7/2009 | Heaton | A61F 7/02 5/284 |
| 2010/0071127 | A1 * | 3/2010 | Koger | A61G 7/103 5/81.1 HS |
| 2012/0079656 | A1 * | 4/2012 | Lewis | A61F 7/00 5/81.1 R |
| 2015/0135436 | A1 * | 5/2015 | Stryker | A61G 7/05 5/600 |
| 2016/0107733 | A1 * | 4/2016 | Thomson | F04D 25/06 417/53 |
| 2016/0220034 | A1 * | 8/2016 | Looslie | A47C 27/081 |

OTHER PUBLICATIONS

International Preliminary Report on Patentability for International Application No. PCT/US2016/013418, dated Jul. 18, 2017, 9 pages.

* cited by examiner

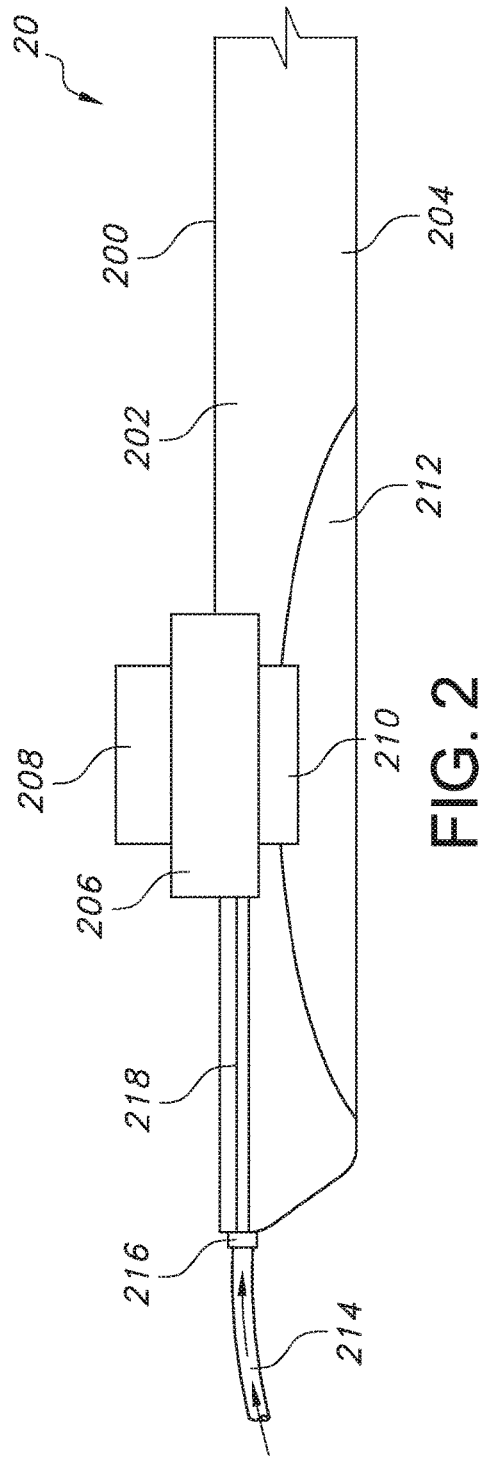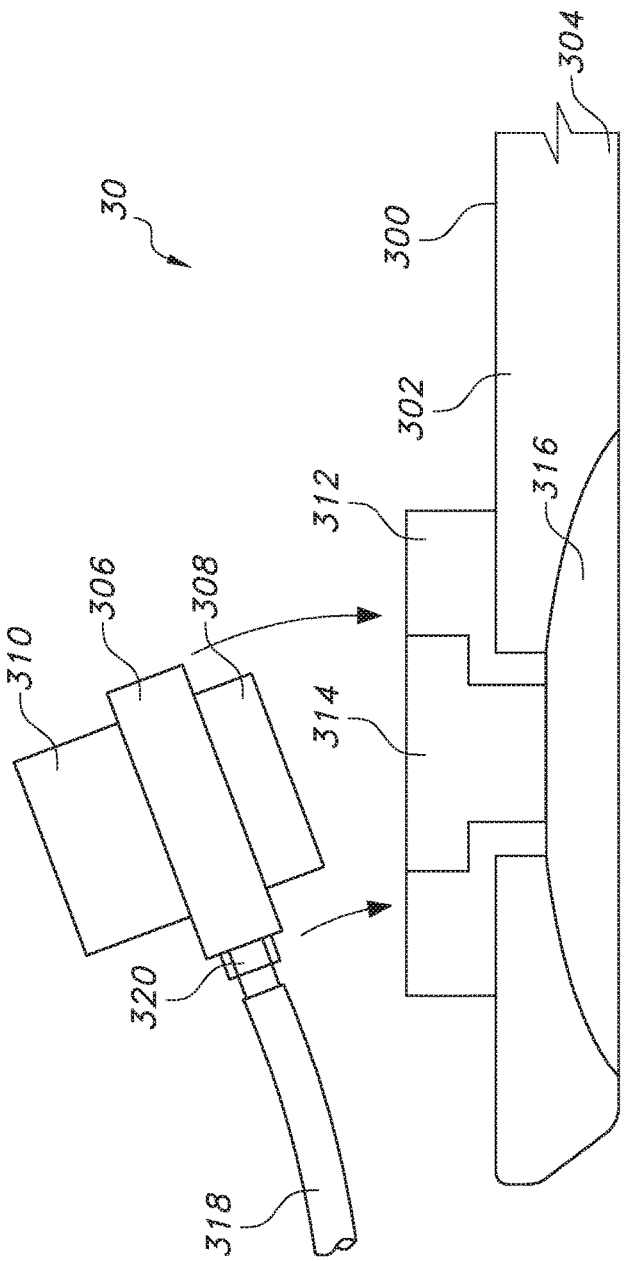

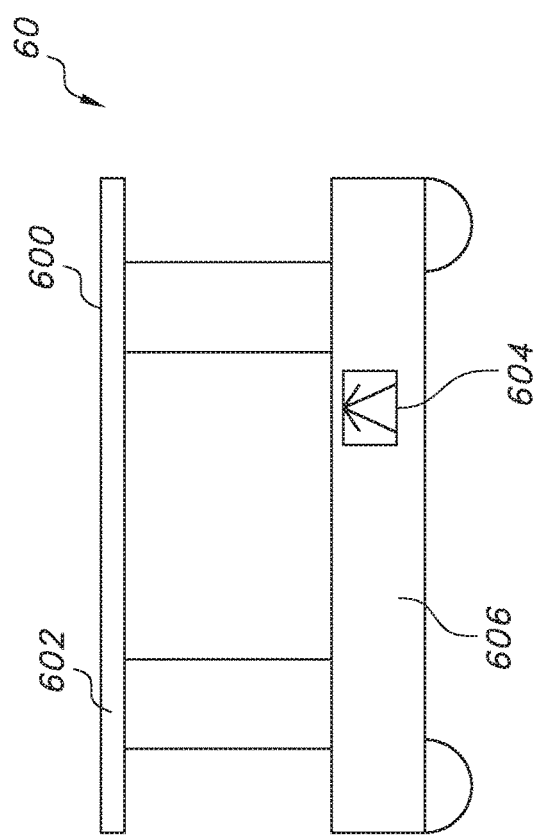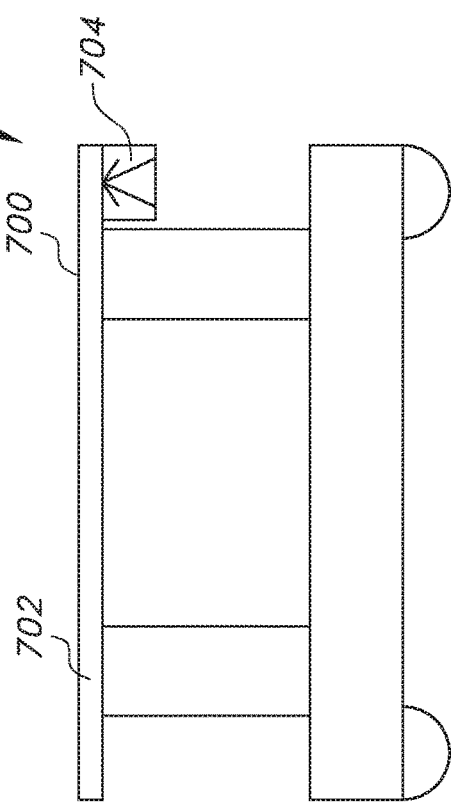

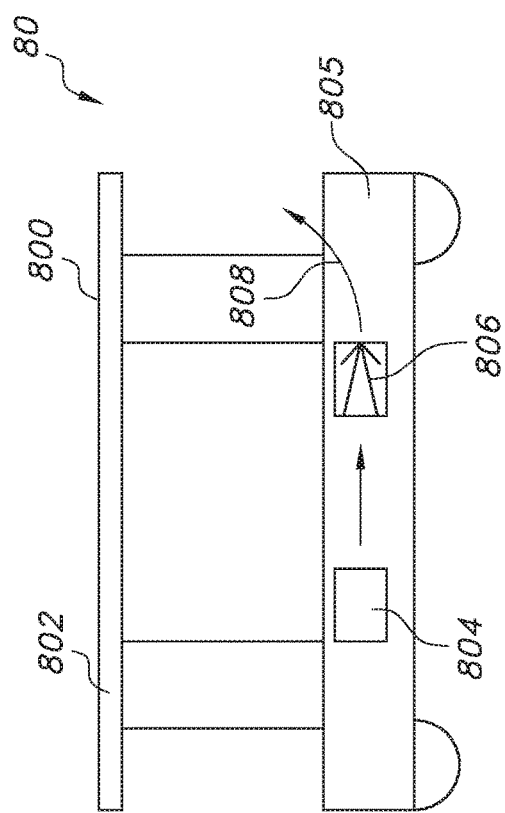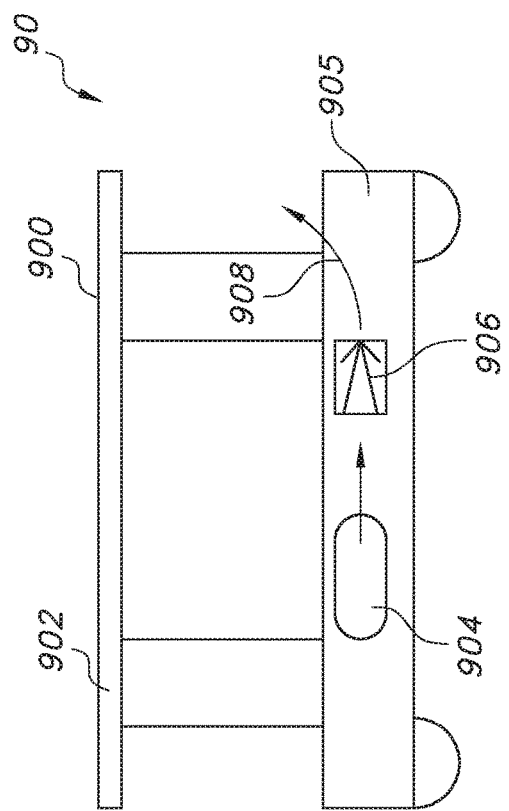

USE OF HIGH PRESSURE LOW VOLUME AIR CONVERSION TO LOW PRESSURE HIGH VOLUME AIR TO POWER PATIENT TRANSPORT DEVICES

CROSS-REFERENCE TO RELATED APPLICATION

This application is the U.S. national phase application of PCT Application No. PCT/US2016/013418, filed Jan. 14, 2016 which is related to and claims the benefit of U.S. Provisional Application No. 62/103,805, filed on Jan. 15, 2015, the entire disclosures of which are incorporated herein by reference.

FIELD OF THE INVENTION

The present invention relates to support surfaces that utilize air flow for various functions.

BACKGROUND OF THE INVENTION

It is often beneficial to have a gas source, such as air, available in locations associated with patient care. For example, hospitals and imaging rooms are usually equipped with low volume high pressure air sources.

However, such air sources are not always suited for applications such as patient transport, patient immobilization, and patient imaging. Also, there are disadvantages associated with alternative air sources such as compressors and the like, especially in settings in which patient imaging is conducted.

Thus, there exists a need for improved air supply systems and methods to enable the use of patient transport or patient immobilization systems, for example, particularly during imaging of patients.

SUMMARY OF THE INVENTION

Aspects of the invention include a system for patient support, patient imaging, patient therapeutic procedures with or without the use of instruments, and patient transport. The system includes a modality with a support surface configured to support a patient thereon, a converter associated with the modality, the converter being configured to receive relatively low-volume high-pressure air from a source of the relatively low-volume high-pressure air and to convert the relatively low-volume high-pressure air into relatively high-volume low-pressure air, and an air flow device configured to receive the relatively high-volume low-pressure air from the converter and provide an air flow function to the modality using the relatively high-volume low-pressure air.

Further aspects of the Invention include a method of supporting a patient. The method includes converting relatively low-volume high-pressure air from a relatively low-volume high-pressure air source into relatively high-volume low-pressure air, receiving, at an air flow device, the relatively high-volume low-pressure air, and providing, with the air flow device, an air flow function to the modality with the relatively high-volume low-pressure air.

BRIEF DESCRIPTION OF THE DRAWINGS

The invention is best understood from the following detailed description when read in connection with the accompanying drawings, with like elements having the same reference numerals. When a plurality of similar elements is present, a single reference numeral may be assigned to the plurality of similar elements with a small letter designation referring to specific elements. Included in the drawings are the following figures:

FIG. 2 is a cross-sectional view of a support surface in accordance with aspects of the invention;

FIG. 3 is a cross-sectional view of a support surface according to aspects of the invention;

FIGS. 6, 7, 8, and 9 are cross-sectional views of modalities in accordance with aspects of the invention;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 10B:
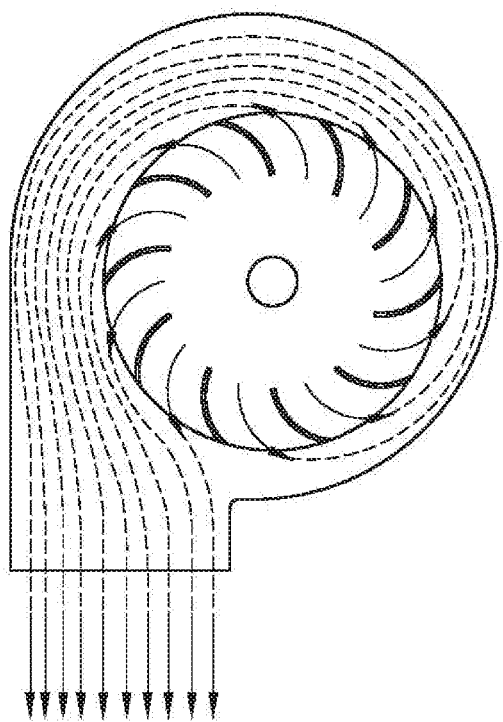
FIGS. 10A, 10B, and 10C are examples of rotary high volume low pressure blowers.
Figure 10A:
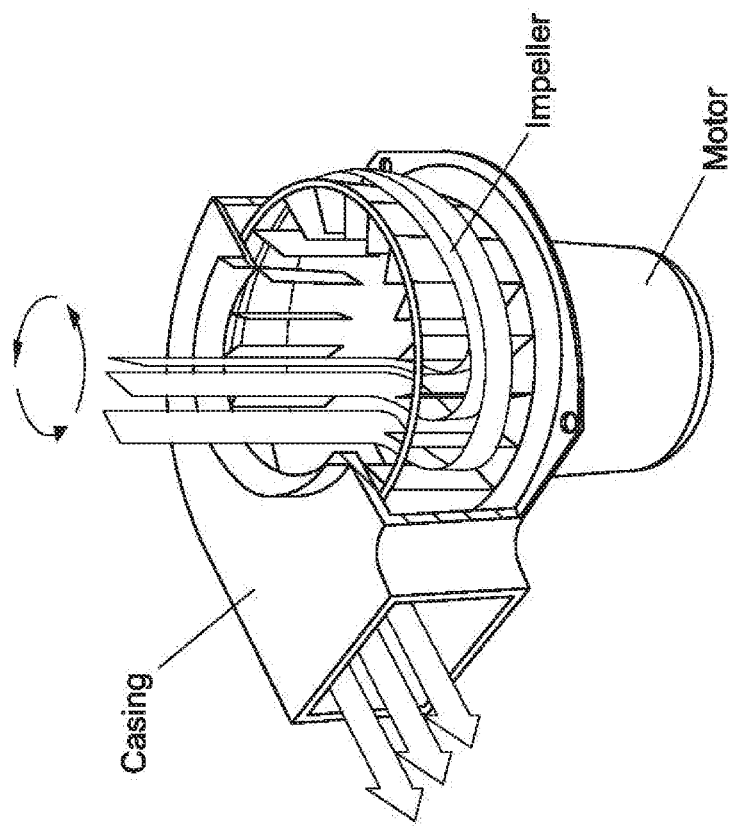
Figure 10C:
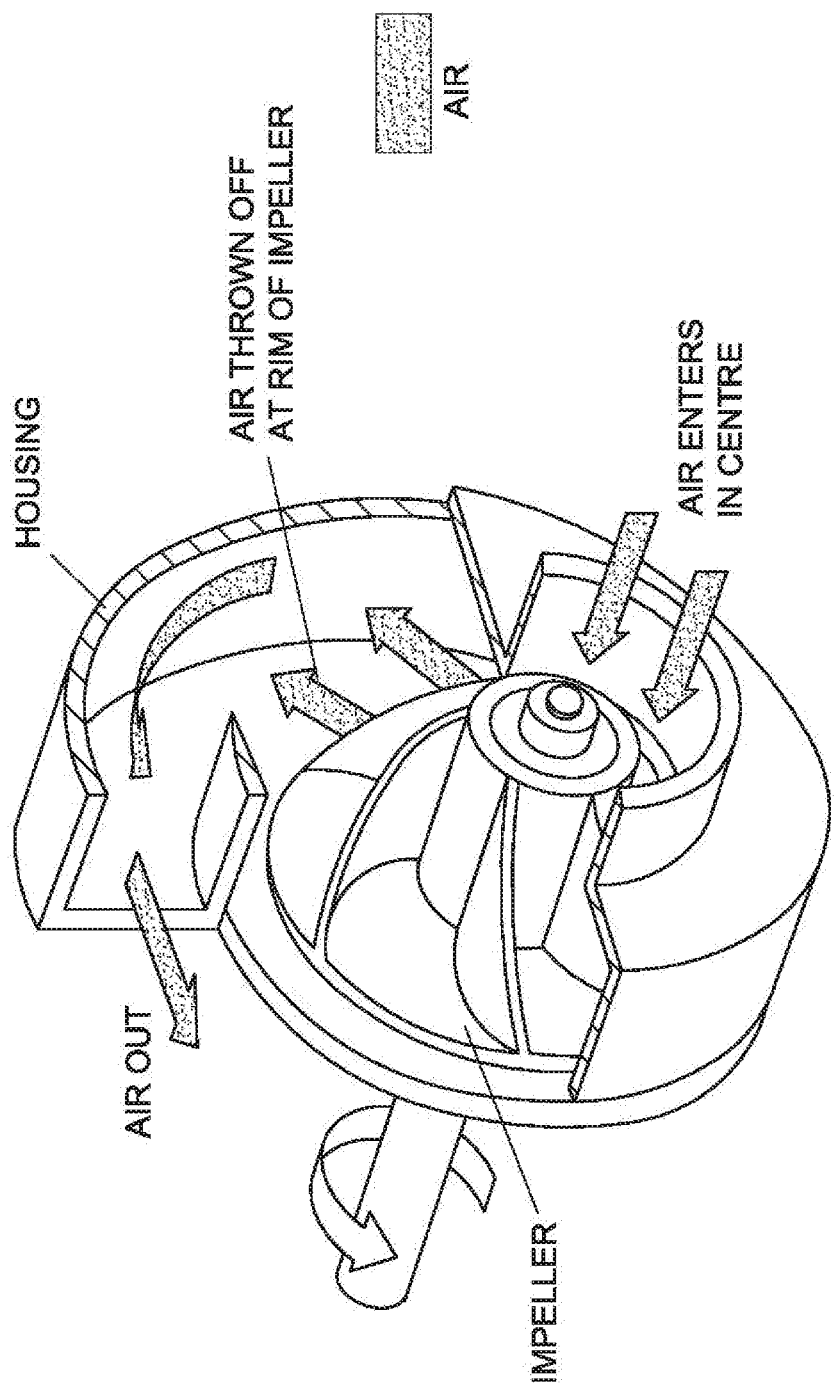

Low volume high pressure air sources are not always suited for applications such as patient transport or patient immobilization. These types of applications typically use high volume low pressure air for the purpose of operating an air bearing, an inflatable pillow, or an air bladder, for example. In order to provide a high volume low pressure flow of air, electric blowers, such as those illustrated in FIGS. 10A, 10B, and 10C can be utilized; however, because these blowers are made from ferromagnetic materials, their use in the vicinity of patient imaging equipment, such as MRI machines, can result in potentially hazardous situations for both patients and MRI machines.

Referring to the figures generally, systems 10, 20, 30, 40, 50, 60, 70, 80, and 90 for providing air flow functions with relatively high volume low pressure air are disclosed in accordance with aspects of the invention. The systems typically include a modality. Modalities include any device associated with patient support, patient imaging, patient therapeutic procedures with or without the use of instruments, and patient transport. The systems also include converters. "Converter" as used herein means a mechanism adapted to convert relatively high pressure low volume air from an air source into relatively high volume low pressure air. The high volume low pressure air is then supplied to an air flow device. Examples of air flow devices include low air loss surfaces, air bearings, air bladders, vacuums, etc.

The air flow devices, when receiving the high volume low pressure air, provide an air flow function to the modality. The air flow functions include, for example, patient transport via air bearings, patient immobilization, wound therapy or breathing control via inflated or vacuumed wraps, body temperature control via openings in a low air loss surface, etc.

Figure 1A:
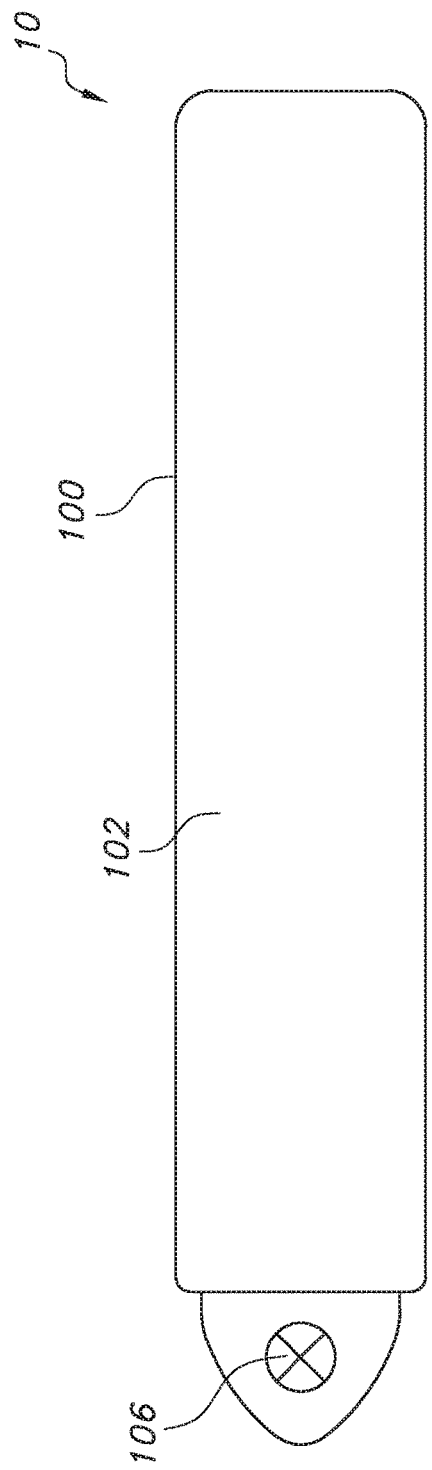
FIGS. 1A and 1B are diagrams of a support surface according to aspects of the invention.
Figure 1B:
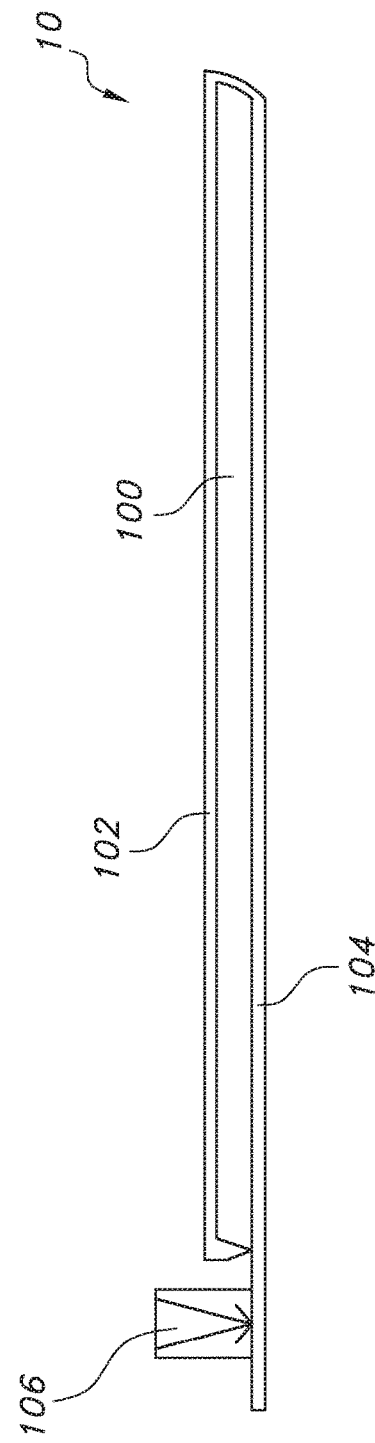

The converters (along with the other components of the systems) may be MRI conditional and/or MRI safe. The converters may be constructed from materials and designed such that they are MRI conditional or MRI safe. This allows the air flow function to be provided within the vicinity of an MRI machine Referring specifically to FIGS. 1A and 1B, views of a system 10 with a support surface 100 are shown according to a first embodiment of the present invention. The support surface 100 includes a top surface 102 and a bottom surface 104, as well as a converter port 106. The support surface 100 may be a patient support surface configured to support a patient on the top surface 102. For example, the support surface 100 may be configured to support a patient for patient imaging, such as magnetic resonant imaging (MRI), x-ray imaging, etc. The support surface 100 may be adapted for movement in order to transfer a patient between modalities. Examples of modalities include trolleys for patient transport, hospital beds, imaging surfaces, etc. Those of skill in the art will recognize other types of modalities will be suitable for use with the support surfaces disclosed herein.

According to various embodiments of the systems disclosed herein, the bottom surface 104 of the support surface 100 may be placed on a modality, may be removably attached to a modality, or may be integrated into a modality, for example. The support surface 100 may be constructed from a variety of materials. For example, the support surface 100 may be constructed of non-ferromagnetic materials (e.g., aluminum), such that the support surface is "MRI conditional." The term "MRI conditional" as used herein refers to configurations and/or designs deemed MRI Conditional as defined in ASTM F2119-07. Alternatively, the support surface 100 may be constructed of materials, such that the support surface is "MRI safe." The term "MRI safe" as used herein refers to configurations and/or designs deemed MRI Safe as defined in ASTM F2119-07. Examples of materials that are "MRI safe" Include polymers (e.g., plastics) and ceramics. The converter port 106 is adapted to receive an air converter so as to supply air flow to the support surface 100 and provide an air flow function to an air flow device associated with the support surface 100. According to the various embodiments of the present invention, the air converter is configured to convert low-volume high-pressure (LVHP) air from an air source into high-volume low pressure (HVLP) air. The converter may be a Venturi blower or other mechanism capable of converting LVHP air into HVLP air. This feature may be easily utilized in, for example, hospital rooms, as a number of hospital rooms are equipped with a low-volume high-pressure air source. Examples of an air flow device include, but are not limited to, low air loss surfaces (e.g. surfaces with openings to control the body temperature of a patient), an air bearing, or a vacuumed wrap (e.g. wraps used to immobilize patients or limit motion). The air flow functions may include, for example, patient transport, inflation of air bearings (e.g., air bladders) coupled to the support surface 100, patient cooling/body temperature control (e.g., via porous support surfaces), vacuum function to remove air between a patient and wrap around the patient to control breathing and movement of a patient receiving treatment (e.g. cancer treatment), and low air loss applications. Low air loss applications may include inflating air cushions having a series of openings that permit the air to slowly escape, thereby providing a constant flow of cool air in the cushion to reduce the body temperature of a patient being supported by the air cushions and the support surface. By converting the air flow into HVLP air, the HVLP air being provided to the air flow devices can be more evenly distributed and/or directed to specific portions of the air flow devices (e.g., directing air flow to the sides of air cushions via openings formed in the sides of the air cushions).

Referring next to FIG. 2, a portion of another system 20 for patient support and imaging is depicted in accordance with aspects of the invention. The system 20 includes a patient support surface 200 with a top surface 202 and a bottom surface 204. A converter 206 for converting LVHP air into HVLP air is integrated into the patient support surface 200. The converter 206 may be constructed of non-ferromagnetic materials, polymer-based materials, and/or other materials such that the converter 206 is MRI conditional or MRI safe. The converter 206 is coupled to an LVHP air source (not shown) via a tube 214, such as an LVHP air source in a hospital room, via a connection port 216 (e.g., a coupling or hose connector) and through a channel 218 embedded in the support surface 200. Alternatively, the channel 218 and coupling 216 may be positioned externally along the top surface 202 of the support surface 200. The converter 206 includes an ambient air inlet portion 208 and an HVLP output 210 which outputs HVLP air to the support surface 200 and provides an air flow function. In the embodiment of the system 20 illustrated in FIG. 2, the HVLP output 210 is positioned to output HVLP air into an air bearing 212 associated with the patient support surface 200 such that the flow of air through the air bearing 212 provides the air flow function, thereby facilitating transport of a patient supported by the support surface 200 between modalities by reducing friction between the support surface 200 and the modalities.

With reference to FIG. 3, a system 30 is depicted in accordance with aspects of the present invention. The system 30 includes a support surface 300 that has a top surface 302 and a bottom surface 304. Integrated into the top surface 302 is a port 312 adapted to receive a converter 306 for converting LVHP air into HVLP air. The converter 306 includes an ambient air inlet portion 310 and an HVLP outlet 308. The converter 306 may be removably inserted into the port 312 such that the HVLP output 308 of the converter 306 is inserted into a channel 314 in the port 312. The channel 314 leads to an air bearing 316 (e.g., an air bladder) coupled to the bottom surface 304 of the support surface 300 such that when the converter 306 is inserted into the port 312, the converter 306 provides HVLP air into the air bearing 316 to provide the air flow function. The converter 306 is connected to an LVHP source (not shown) via tube 318 that is connected by a coupling 320 between the tube 318 and the converter 306. The LVHP air source may be, for example, an LVHP air source in a hospital room.

Although the systems 20 and 30 depicted in FIGS. 2 and 3 depict examples of support surfaces formed with air bearings and to which a converter provides the air function of directing HVLP air into the air bearings, the invention is not intended to be limited to such applications. As described above, the systems 20 and 30 may be adapted such that the air flow function includes, but is not limited to, inflating a bladder, cooling a patient during MR imaging, transporting a patient, low air loss functionality, and providing a vacuum function.

Figure 4:
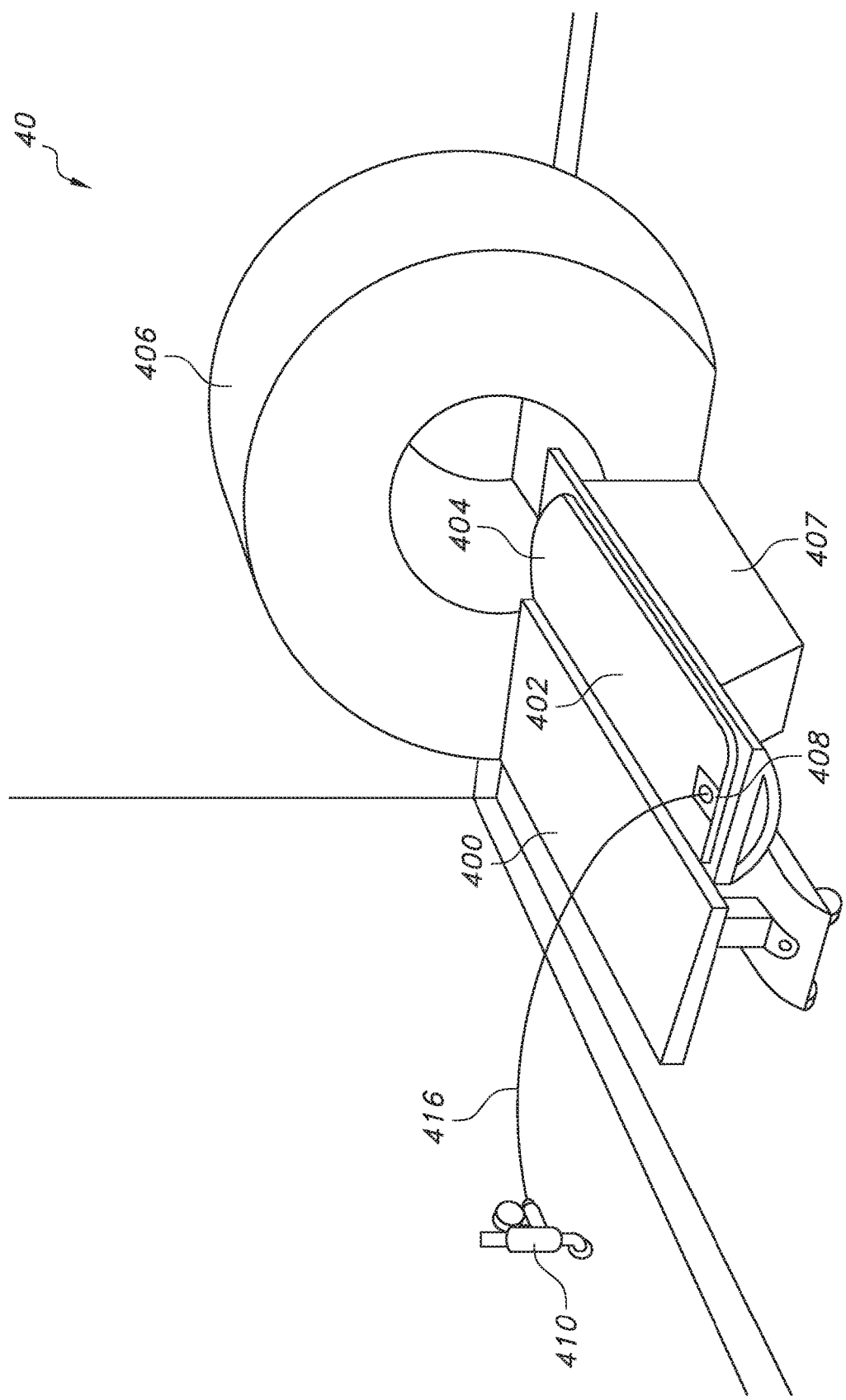
FIG. 4 depicts a system for imaging a patient in accordance with aspects of the invention.

In FIG. 4, a system 40 for imaging a patient according to another embodiment of the present invention is provided. A first modality 400 in the form of a patient trolley is positioned next to a support surface 402 adapted to support a patient thereon during imaging of the patient. The support surface 402 is positioned on a second modality 407 in the form of an imaging table that is used for imaging via an MRI machine 406. In an embodiment, the support surface 402 is configured to be moved between the patient trolley 400 and the imaging table 407 while supporting the patient thereon. A converter 408 is integrated into the top surface 404 of the support surface 402. The converter 408 is connected to an LVHP air source 410 via a connector 416 (e.g., a tube). The converter 408 is configured to convert the LVHP air from the air source 410 into HPLV air so as to provide an air flow function to the support surface 402, the trolley 400, and/or the imaging table 407. In one embodiment, the air flow function may include providing air to an air bearing formed on the support surface 402 such that the support surface 402 can be easily transferred between the trolley 400 and the imaging table 402 while supporting a patient thereon. It is contemplated that other air flow functions may be provided by the converter 408. For example, the air flow function may be cooling the patient, pulling air by a vacuum function through a wrap over a patient for patient immobilization, breathing control, etc. The converter 408, support surface 402, and other components may be constructed to be MRI conditional or comprising MRI safe materials (e.g., polymers, ceramics, etc.).

Figure 5:
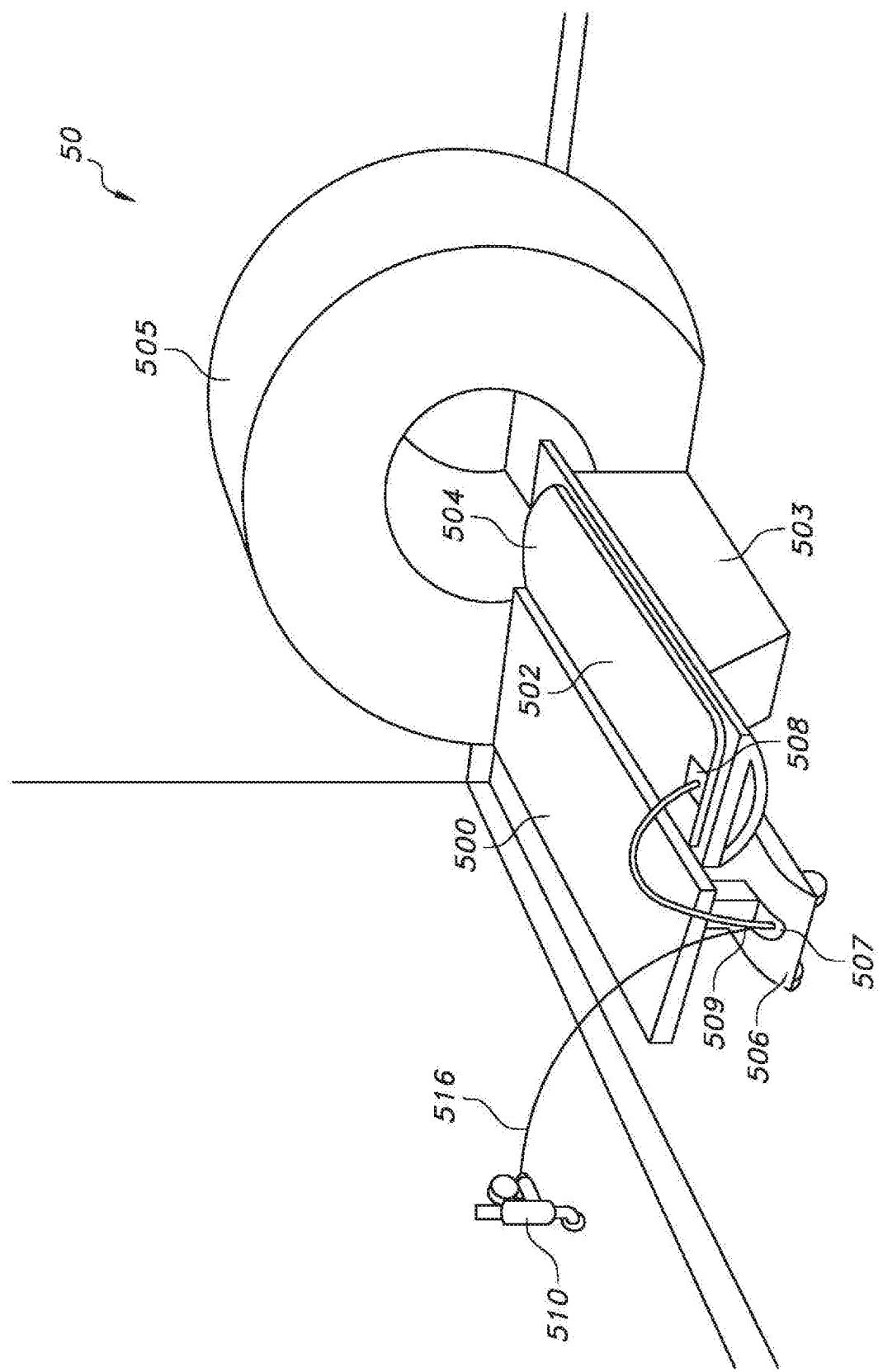
FIG. 5 depicts a system for imaging a patient according to aspects of the invention.

Another system 50 is depicted in FIG. 5 according to aspects of the present invention. A trolley 500 is positioned next to a support surface 502 that is positioned on an imaging table 503 adapted for MRI imaging via the MRI machine 505. In system 50, a Converter 507 for converting LVHP air into HVLP air is integrated into the base of the trolley 506. A port 508 in the support surface 502 is connected to an output of the converter 507 via a tube 509 and is configured to either receive the HVLP air from the converter 507 or draw air to provide a vacuum function such that the converter 507 provides an air flow function to the support surface 502, such as those air flow functions described above. An Input of the converter 507 may be connected to a LVHP air source 510 via a connector 516. When activated, the converter 507 receives the LVHP air from the air source 510, converts the LVHP air into HVLP air, and either supplies the HVLP air into the port 508 on the support surface 502 via the tube 509 or draws air from the port 508 through the tube 509 to provide a vacuum function, thereby providing an air flow function to the support surface 502. The converter 507, support surface 502, port 508, and other components may be constructed to be MRI conditional or comprising MRI safe materials (e.g., polymers, ceramics, etc.).

In the systems 40 and 50 shown at FIGS. 4 and 5, various arrangements may be utilized. The converters may be integrated into the trolleys and/or support surfaces, or the converters may be removably attached to the trolleys and/or support surfaces. It is contemplated that the converters may be integrated into the imaging tables. The converters may be attached directly to the air source and connected via tubes, hoses, or lines to ports formed on the trolleys, support surfaces, imaging tables, etc. As would be understood by those of skill in the art, various other configurations are possible in addition to the embodiments disclosed herein.

Various systems 60, 70, 80, and 90 are depicted in FIGS. 6-9 in accordance with aspects of the invention. System 60 includes a modality 600 in the form of a patient trolley having a patient support surface 602. The modality 600 includes a converter 604 positioned in the base 606 of the modality 600 that is adapted to convert LVHP air into HVLP air and provide an air flow function to the modality 600. Alternatively, the base 606 may include a port, such as the ports described above, to receive an HVLP air flow source. System 70 includes a modality 700 with a top surface 702. The modality 700 includes a converter 704 positioned on the underside of the top surface 702 that is adapted to convert LVHP air into HVLP air and provide an air flow function to the modality 700. Alternatively, the top surface 702 may include a port such as the ports described above to receive an HVLP air flow source. It is contemplated that systems according to various embodiments of the present invention may include trolleys having one or more converters/ports at various other locations.

System 80 includes a modality 800 with a top surface 802 and a base 805. Integrated into the base is a high pressure air compressor 804 that is adapted to output high pressure air into a converter 806. The converter 806 converts the high pressure air into HPLV air 808 such that it can be outputted to supply the HPLV air to the modality 800 and provide an air flow function. System 90 includes a modality 900 with a top surface 902 and a base 905. Integrated into the base is a high pressure air tank 904 configured to supply high pressure air into a converter 906. The converter 906 converts the high pressure air from the tank 904 into HPLV air 908 and outputs the HPLV air 908 to supply an air flow function to the modality 900. The systems 60, 70, 80, and 90 may alternatively be configured to provide an air flow function to an external device, such as a support surface, other modality, imaging device, etc.

Figure 11:
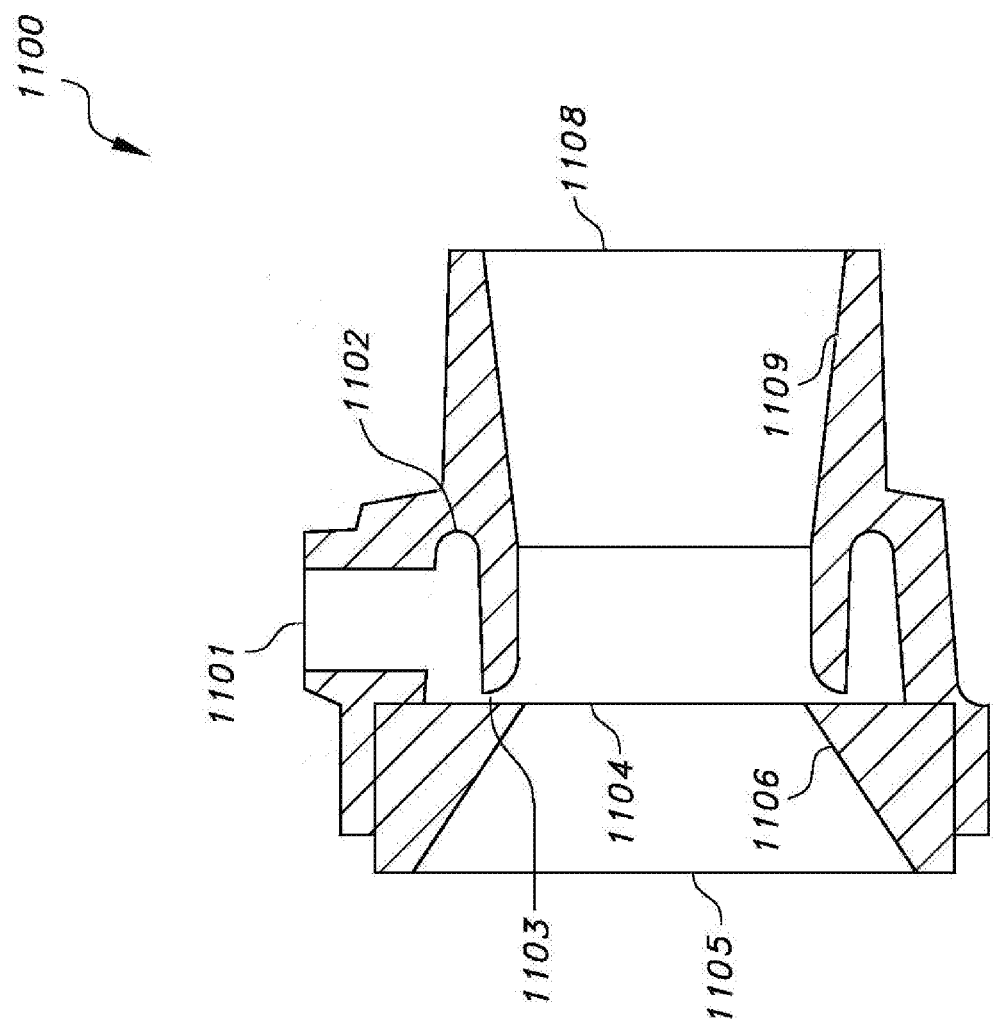
FIG. 11 is a cross-sectional view of a converter in accordance with aspects of the invention.

An embodiment of a converter that may be incorporated into the various systems according to the present invention is illustrated in FIG. 11. A cross-sectional view of a converter 1100 is depicted. The converter 1100 has an air supply input 1101 for receiving relatively HPLV air. The air is delivered from the input to an annular space 1102 and subsequently forced through a narrow section 1103 of the annular space 1102 that is in fluid connection with the exhaust portion 1108 of the converter 1100. The narrow section 1103 is adjacent to an inner face 1104 of an ambient gas inlet 1105. The high velocity of the HPLV air flowing through the narrow section 1103 expands through the exhaust portion 1108 and draws the ambient air through the gas inlet 1105 such that the air flowing through the exhaust portion 1108 is relatively LPHV air and a vacuum function is provided at the ambient gas inlet 1105. As would be appreciated by one of skill in the art, the flow rate and pressure of the air flowing through the converter 1100 may be modified by changing the dimensions and/or geometry of one or more of the features of the converter 1100, such as the inner channel 1106 of the ambient gas inlet 1105 or the Inner channel of the exhaust portion 1108.

Further aspects of the invention include methods for providing air flow functions. The methods first include converting LVHP air into HVLP air. The LVHP air may be converted with a converter, such as a venturi blower, and/or other devices capable of such air conversion. In an embodiment, the converter is constructed to be MRI conditional or comprising MRI safe materials.

The converted air may then be supplied to an air flow device. The converted air may be directly supplied from a converter integrated into the modality or a converter removably attached to the modality, for example. The converted air may also be supplied via tubes or other connecters when the converter is utilized externally from the modality.

The air flow device then provides an air flow function. In one example where the air flow device is an air bearing, the air flow function may be patient/support surface transport. In another example where the air flow device is a low air loss surface, the air flow function may be used for body temperature control.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A system for at least one of patient support, patient imaging, patient therapeutic procedures with or without the use of instruments, and patient transport, the system comprising:
   a modality with a support surface configured to support a patient thereon;
   a converter associated with the modality, the converter not comprising an electric blower, the converter being configured to receive relatively low-volume high-pressure air flow from a source of the relatively low-volume high-pressure air flow and to draw ambient air, and thereby to convert the relatively low-volume high-pressure air flow and the ambient air into relatively high-volume low-pressure air flow; and
   an air flow device configured to receive the relatively high-volume low-pressure air flow from the converter and provide an air flow function to the modality using the relatively high-volume low-pressure air flow.

2. The system of claim 1, wherein the air flow device is configured to direct the relatively high-volume low-pressure air flow toward the support surface of the modality, thereby facilitating transfer of the patient to or from the modality.

3. The system of claim 2, wherein the air flow device is configured to provide an air bearing positioned below the support surface of the modality.

4. The system of claim 1, wherein the air flow device is coupled to the modality.

5. The system of claim 1, wherein the converter is constructed of non-ferromagnetic material.

6. The system of claim 5, wherein the converter is constructed of a polymer-based material.

7. The system of claim 1, wherein the converter is integrated into the modality.

8. The system of claim 1, wherein the converter is removably connected to the modality.

9. The system of claim 1, wherein the modality, the converter, and the air flow device are constructed of materials such that the system is MRI safe.

10. A method of providing air flow to a modality, the method comprising:
    converting relatively low-volume high-pressure air flow from a relatively low-volume high-pressure air flow source and ambient air into relatively high-volume low-pressure air flow;
    receiving, at an air flow device, the relatively high-volume low-pressure air flow; and
    providing, with the air flow device, an air flow function to the modality with the relatively high-volume low-pressure air flow,
wherein the converting step does not utilize an electric blower.

11. The method of claim 10, wherein the providing step further comprises supplying air flow toward the support surface of the modality to facilitate transfer of the patient to or from the modality as the air flow function.

12. The method of claim 10, wherein the providing step further comprises inflating an air bladder positioned below the support surface of the modality to facilitate transfer of the patient to or from the modality as the air flow function.

13. The method of claim 10, further comprising imaging the patient with an MRI device, wherein the converter is constructed of a non-ferromagnetic material.

14. The method of claim 13, wherein the converter is constructed of a polymer-based material.

15. The method of claim 10, further comprising coupling the converter to the relatively low-volume high-pressure air source.

16. The method of claim 10, further comprising coupling the converter to the modality.

17. The system of claim 2, wherein the air flow device is configured to provide a low air loss cushion to control body temperature of a patient.

18. The system of claim 2, wherein the air flow device is configured to provide a vacuumed wrap around the body of a patient.

19. The method of claim 10, wherein the providing step further comprises inflating a low air loss cushion to control body temperature of a patient.

20. A method of providing an air flow function to a modality, the method comprising:
    converting relatively low-volume high-pressure air flow from a relatively low-volume high-pressure air flow source into relatively high-volume low-pressure air flow through a converter;
    expelling the relatively high-volume low-pressure air flow through an outlet of the converter and generating a vacuum function at an inlet of the converter; and
    vacuuming air from an air flow device coupled to the inlet of the converter, the air flow device being associated with the modality,
wherein the converting step does not utilize an electric blower.

21. A system for at least one of patient support, patient imaging, patient therapeutic procedures with or without the use of instruments, and patient transport, the system comprising:
    a modality with a support surface configured to support a patient thereon;
    an air flow device configured to receive relatively high-volume low-pressure air flow and to provide an air flow function to the modality using the relatively high-volume low-pressure air flow; and
    a converter configured to convert relatively low-volume high-pressure air flow to the relatively high-volume low-pressure air flow, the converter comprising:
        an air inlet configured to receive the relatively low-volume high-pressure air flow from a source,
        an ambient air inlet configured to draw ambient air, and
        an exhaust outlet configured to deliver the relatively high-volume low-pressure air flow to the air flow device,
wherein the converter is configured to receive the relatively high-pressure low-volume air flow from the source, thereby drawing the ambient air through the ambient air inlet as a result of a negative pressure difference between the relatively low-pressure high-volume air flow and the ambient air, thereby creating the relatively high-volume low-pressure air flow.

22. The system according to claim 1, wherein the converter defines an air supply input positioned to receive the relatively low-volume high-pressure air flow, an exhaust outlet positioned to deliver the relatively high-volume low-pressure air flow toward the air flow device from the source of the relatively low-volume high-pressure air flow, and an ambient air inlet positioned between the air supply input and the exhaust outlet;

wherein the ambient air inlet is configured to draw the ambient air into the converter and to direct the ambient air toward the exhaust outlet; and wherein the ambient air inlet, the air supply input and the exhaust outlet are all in fluid communication.

\* \* \* \* \*